United States Patent
Ananthapadmanabhan et al.

(10) Patent No.: US 9,242,002 B2
(45) Date of Patent: *Jan. 26, 2016

(54) ANTI-DANDRUFF SHAMPOO

(75) Inventors: Kavssery Parameswaran Ananthapadmanabhan, Trumbull, CT (US); Caroline Alexandra Hall, Wirral (GB); Albert Joseph Post, Trumbull, CT (US); Georgia Shafer, Trumbull, CT (US); Graham Andrew Turner, Wirral (GB); Aneliya Nikolova Zdravkova, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 122 days.

This patent is subject to a terminal disclaimer.

(21) Appl. No.: 13/816,265

(22) PCT Filed: Jul. 14, 2011

(86) PCT No.: PCT/EP2011/062043
§ 371 (c)(1),
(2), (4) Date: Mar. 1, 2013

(87) PCT Pub. No.: WO2012/022553
PCT Pub. Date: Feb. 23, 2012

(65) Prior Publication Data
US 2013/0150338 A1   Jun. 13, 2013

(30) Foreign Application Priority Data
Aug. 18, 2010   (EP) .................................... 10173221

(51) Int. Cl.
*A61K 8/00* (2006.01)
*A61K 8/18* (2006.01)
*A61Q 5/00* (2006.01)
*A61Q 9/00* (2006.01)
*A61K 8/30* (2006.01)
*A61K 47/20* (2006.01)
*A61K 8/27* (2006.01)
*A61K 8/36* (2006.01)
*A61K 8/44* (2006.01)
*A61K 8/46* (2006.01)
*A61Q 5/02* (2006.01)
*A61Q 5/12* (2006.01)
*A61Q 19/00* (2006.01)
*A61K 31/555* (2006.01)

(52) U.S. Cl.
CPC . *A61K 47/20* (2013.01); *A61K 8/27* (2013.01); *A61K 8/361* (2013.01); *A61K 8/44* (2013.01); *A61K 8/442* (2013.01); *A61K 8/463* (2013.01); *A61K 8/466* (2013.01); *A61K 31/555* (2013.01); *A61Q 5/006* (2013.01); *A61Q 5/02* (2013.01); *A61Q 5/12* (2013.01); *A61Q 19/00* (2013.01)

(58) Field of Classification Search
USPC ............................................... 424/70.1, 70.24
See application file for complete search history.

(56) References Cited

U.S. PATENT DOCUMENTS

| | | |
|---|---|---|
| 3,723,325 A | 3/1973 | Parran, Jr. |
| 3,958,581 A | 5/1976 | Abegg |
| 3,962,418 A | 6/1976 | Birkofer |
| 4,009,256 A | 2/1977 | Nowak |
| 4,089,945 A | 5/1978 | Brinkman et al. |
| 4,554,207 A | 11/1985 | Lee |
| 4,565,647 A | 1/1986 | Llenado |
| 4,654,207 A | 3/1987 | Preston |
| 4,741,855 A | 5/1988 | Grote et al. |
| 5,009,814 A | 4/1991 | Kelkenberg et al. |
| 5,132,037 A | 7/1992 | Greene et al. |
| 5,194,639 A | 3/1993 | Connor |
| 5,234,619 A | 8/1993 | Greene et al. |
| 5,290,471 A | 3/1994 | Greene et al. |
| 5,372,751 A | 12/1994 | Rys-Cicciari et al. |
| 5,389,279 A | 2/1995 | Au et al. |
| 5,415,610 A | 5/1995 | Schutz et al. |
| 5,415,810 A | 5/1995 | Lee |
| 5,612,307 A | 3/1997 | Chambers et al. |
| 5,641,480 A * | 6/1997 | Vermeer .................... 424/70.24 |
| 5,703,026 A | 12/1997 | Setser et al. |
| 5,716,919 A | 2/1998 | Sano |
| 5,739,365 A | 4/1998 | Briody et al. |
| 5,804,540 A | 9/1998 | Tsaur et al. |

(Continued)

FOREIGN PATENT DOCUMENTS

| | | |
|---|---|---|
| DE | 10059819 | 6/2002 |
| DE | 10059825 | 6/2013 |

(Continued)

OTHER PUBLICATIONS

Denkov et al., Wall slip and viscous dissipationin sheared foams: Effect of surface mobility, J. Colloids and Surfaces A, Jan. 23, 2005, 129-145, 263, Elsevier, US.
Coconut Oil, Coconut Oil Wikipedia, pp. 1-10, XP002638078.
"Anionic surfactant for the detergent industry", Clariant Genapoll LRO Liquid, Jan. 2010, p. 1, XP-002637790.
"Amphoteric surfactant for the cosmetic industry", Clariant Genagen CAB, Aug. 2008, pp. 1-2, XP002637791.
Co-pending Application: Applicant: Hall et al, U.S. Appl. No. 13/816,253, filed Mar. 1, 2013.
Notice of Opposition in EP26005833 (EP11736324) (Procter & Gamble)pposition, Sep. 5, 2014, 28, EP.

*Primary Examiner* — Layla Soroush
(74) *Attorney, Agent, or Firm* — Ronald A. Koatz

(57) ABSTRACT

The invention relates to an anti-dandruff shampoo comprising: —a) from 0.1 to 5 wt. % of an anti-dandruff zinc salt; b) from 1 to 8 wt. % of an alkyl glycinate and/or alkyl carboxyglycinate; c) from 2 to 16 wt. % of an alkyl sulphate and/or an ethoxylated alkyl sulfate anionic surfactant; and, d) from 1 to 10 wt. % of a fatty acyl isethionate product which product comprises 40 to 80 wt. % fatty acyl isethionate and 15 to 50 wt. % free fatty acid and/or fatty acid salt and to the use of a surfactant system comprising components b) to d) to provide an improvement to the skin stratum corneum barrier.

9 Claims, No Drawings

(56) References Cited

U.S. PATENT DOCUMENTS

| | | |
|---|---|---|
| 5,952,286 A | 9/1999 | Puvvada et al. |
| 5,965,500 A | 10/1999 | Puvvada |
| 5,985,500 A | 11/1999 | Fuller et al. |
| 6,071,866 A | 6/2000 | Fujiwara et al. |
| 6,077,816 A | 6/2000 | Puvvada et al. |
| 6,429,177 B1 | 8/2002 | Williams et al. |
| 6,730,643 B2 | 5/2004 | Chokappa et al. |
| 6,906,016 B1 | 6/2005 | Tsaur |
| 6,926,900 B1 | 8/2005 | Maurin |
| 7,084,104 B2 | 8/2006 | Martin et al. |
| 7,098,180 B2 | 8/2006 | Ganopolsky et al. |
| 7,119,059 B2 | 10/2006 | Librizzi et al. |
| 7,279,154 B2 | 10/2007 | Loffler et al. |
| 7,332,155 B2 | 2/2008 | Loffler et al. |
| 7,547,752 B2 | 6/2009 | Bailey et al. |
| 7,655,607 B2 | 2/2010 | Tsaur et al. |
| 7,659,235 B2 | 2/2010 | Tsaur et al. |
| 7,671,000 B2 | 3/2010 | Tsaur et al. |
| 7,674,759 B2 | 3/2010 | Tsaur et al. |
| 7,807,612 B2 | 10/2010 | Tsaur |
| 8,105,994 B2 | 1/2012 | Tsaur |
| 8,119,168 B2 | 2/2012 | Johnson et al. |
| 8,124,574 B2 | 2/2012 | Tsaur et al. |
| 8,263,538 B2 | 9/2012 | Tsaur |
| 8,268,767 B2 | 9/2012 | Tsaur |
| 2002/0037299 A1 | 3/2002 | Turowski-Wanke et al. |
| 2002/0102228 A1 | 8/2002 | Dunlop et al. |
| 2004/0109835 A1 | 6/2004 | Loffler et al. |
| 2004/0224863 A1 | 11/2004 | Sun |
| 2005/0075256 A1 | 4/2005 | Librizzi |
| 2005/0089536 A1 | 4/2005 | Loffler et al. |
| 2005/0100570 A1 | 5/2005 | Wei et al. |
| 2005/0136026 A1 | 6/2005 | Qiu et al. |
| 2005/0143268 A1 | 6/2005 | Midha |
| 2005/0192188 A1 | 9/2005 | Wagner et al. |
| 2006/0079420 A1 | 4/2006 | Wagner |
| 2007/0066501 A1 | 3/2007 | Yang et al. |
| 2007/0081953 A1 | 4/2007 | Dahms |
| 2007/0128147 A1 | 6/2007 | Schwartz et al. |
| 2008/0153727 A1 | 6/2008 | Tsaur et al. |
| 2008/0153729 A1 | 6/2008 | Tsaur |
| 2008/0153730 A1 | 6/2008 | Tsaur |
| 2009/0062177 A1 | 3/2009 | Tsaur |
| 2009/0062406 A1 | 3/2009 | Loeffler |
| 2009/0156450 A1 | 6/2009 | Tsaur |
| 2010/0210500 A1 | 8/2010 | Liu et al. |
| 2011/0086789 A1 | 4/2011 | Tsaur et al. |
| 2011/0118162 A1 | 5/2011 | Shiloach et al. |

FOREIGN PATENT DOCUMENTS

| | | |
|---|---|---|
| EP | 0285388 | 10/1988 |
| EP | 0559375 A1 | 9/1993 |
| EP | 1029532 A1 | 8/2000 |
| EP | 1069142 A1 | 1/2001 |
| EP | 1479365 A1 | 11/2004 |
| EP | 1237534 B1 | 1/2005 |
| GB | 2015561 | 9/1979 |
| JP | 63243200 | 10/1988 |
| WO | WO9206154 A1 | 4/1992 |
| WO | WO9522311 | 8/1995 |
| WO | WO9705857 | 2/1997 |
| WO | WO9726854 | 7/1997 |
| WO | WO9811864 | 3/1998 |
| WO | WO9827193 | 6/1998 |
| WO | WO9932069 | 7/1999 |
| WO | WO0021492 | 4/2000 |
| WO | WO0243689 | 6/2002 |
| WO | WO03017968 A2 | 3/2003 |
| WO | WO03088957 A1 | 10/2003 |
| WO | WO2004035015 A1 | 4/2004 |
| WO | WO2005046629 A1 | 5/2005 |
| WO | WO2007130390 A2 | 11/2007 |
| WO | WO2007144189 | 12/2007 |
| WO | WO2008074617 A1 | 6/2008 |
| WO | WO2009030594 A1 | 3/2009 |
| WO | WO2009063250 | 5/2009 |
| WO | WO2009077495 A2 | 6/2009 |
| WO | WO2010034721 | 4/2010 |
| WO | WO2010046354 A2 | 4/2010 |
| WO | WO2011045191 A2 | 4/2011 |
| WO | WO2012022553 | 2/2012 |
| WO | WO2012072424 | 12/2012 |

* cited by examiner

ANTI-DANDRUFF SHAMPOO

The invention relates to an anti-dandruff shampoo composition that provides improvement in the condition of the skin stratum corneum barrier.

Dandruff is an issue that affects many people globally. The condition is manifested by the shedding of clumps of dead skin cells from the scalp. These are white in colour and provide an aesthetically displeasing appearance. Factors that contribute to dandruff are certain members of the *Malassezia* yeasts. To combat these, anti-dandruff products have included certain zinc salts which have anti-fungal activity, for example zinc pyrithione (ZnPTO). Such a product has to perform as a hair cleansing shampoo, while mitigating the causes of dandruff. An example of a known anti-dandruff shampoo comprises sodium lauryl ether sulfate (an ethoxylated anionic surfactant) in combination with zinc pyrithione.

An alternative approach to mitigating the cause of dandruff is to improve the skin stratum corneum barrier condition, that way the scalp becomes more resistant to the causes of dandruff.

WO 2004/035015 A1 discloses a shampoo comprising an anti-dandruff zinc salt, sodium laureth sulphate and conjugated linoleic acid.

It is an object of the invention to provide an anti-dandruff shampoo composition that provides improvement in skin stratum corneum barrier condition.

We have found that the surfactant system comprising: i) an fatty acyl isethionate product which product comprises 40 to 80 wt. % fatty acyl isethionate and 15 to 50 wt. % free fatty acid and/or fatty acid salt; ii) an alkyl glycinate and/or alkyl carboxyglycinate; and, iii) an alkyl sulphate and/or and ethoxylated alkyl sulfate anionic surfactant, provides an improvement to the skin stratum corneum barrier condition.

SUMMARY OF THE INVENTION

The invention thus provides in a first aspect an anti-dandruff shampoo comprising:
a) from 0.1 to 5 wt. % of an anti-dandruff zinc salt;
b) from 1 to 8 wt. % of an alkyl glycinate and/or alkyl carboxyglycinate;
c) from 2 to 16 wt. % of an alkyl sulphate and/or and ethoxylated alkyl sulfate anionic surfactant; and,
d) from 1 to 10 wt. % of a fatty acyl isethionate product which product comprises 40 to 80 wt. % fatty acyl isethionate and 15 to 50 wt. % free fatty acid and/or fatty acid salt.

A second aspect of the invention relates to the use of a surfactant system comprising: i) an fatty acyl isethionate product which product comprises 40 to 80 wt. % fatty acyl isethionate and 15 to 50 wt. % free fatty acid and/or fatty acid salt; ii) an alkyl glycinate and/or alkyl carboxyglycinate; and, iii) an alkyl sulphate and/or and ethoxylated alkyl sulfate anionic surfactant, to provide an improvement to the skin stratum corneum barrier condition.

PREFERRED EMBODIMENTS

The anti-dandruff shampoo comprises an antidandruff zinc salt. The anti-dandruff zinc salts are preferably selected from zinc pyrithione, zinc sulfate and hydrates thereof (e.g. zinc sulfate hexahydrate), and combinations thereof. Zinc pyrithione (ZnPTO) shorthand for zinc 1-hydroxy-2-pyridinethione is most preferred.

The anti-dandruff zinc salt is present at a level of from 0.1 to 5 wt. %, preferably from 0.2 to 3 wt. %, more preferably from 0.25 to 2.5 wt. % based on the shampoo composition.

The anti-dandruff shampoo comprises from 1 to 8 wt. %, preferably from 2 to 6 wt. % of an alkyl glycinate and/or alkyl carboxyglycinate.

Preferably the alkyl glycinate and/or alkyl carboxyglycinate has an alkyl group of from $C_{8-22}$ carbon atoms, in the form of a salt with a solubilising cation such as sodium, potassium, ammonium or substituted ammonium. Preferred glycinates are sodium coco glycinate and sodium cocoyl glycinate.

The anti-dandruff shampoo comprises an alkyl sulphate and/or ethoxylated alkyl sulfate anionic surfactant at a level of from 2 to 16 wt. %, preferably from 3 to 12 wt. %, more preferably from 4 to 10 wt. %.

Preferred alkyl sulfates are $C_{8-18}$ alky sulfates, more preferably $C_{12-18}$ alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES) having an average degree of ethoxylation of from 0.5 to 3, preferably 1 to 3.

The fatty acyl isethionate product is present at a level of from 1 to 10 wt. %, preferably from 2 to 8 wt. %, more preferably from 2.5 to 7.5 wt. %.

The preferred fatty acyl isethionate product comprises fatty acyl isethionate surfactant at a level of from 40 to 80 wt. % of the product, as well as free fatty acid and/or fatty acid salt at a level of from 15 to 50%.

Preferably, greater than 20 wt. % and less than 45 wt. %, more preferably greater than 25 wt. % and less than 45 wt. % of the fatty acyl isethionate are of chain length greater than or equal to $C_{16}$; and greater than 50 wt. %, preferably greater than 60 wt. % of the free fatty acid/soap is of chain length $C_{16}$ to $C_{20}$.

In a preferred embodiment, the anti-dandruff shampoo comprises from 0.1 to 10 wt. %, preferably from 0.5 to 8 wt. %, more preferably from 1 to 5 wt. % of a betaine surfactant, preferably an alkyl amidopropyl betaine, for example cocamidopropyl betaine.

In a further preferred embodiment, the anti-dandruff shampoo comprises from 0.1 to 5 wt. % of a cationic polymer, preferably a cationic polysaccharide polymer.

A particularly preferred embodiment of the invention is an anti-dandruff shampoo comprising:
a) from 0.25 to 2.5 wt. % of zinc pyrithione;
b) from 2 to 6 wt. % of sodium alkyl carboxylglycinate having an alkyl group of from $C_{8-22}$ carbon atoms;
c) from 4 to 10 wt. % of sodium lauryl ether sulfate having an average degree of ethoxylation of from 0.5 to 3;
d) from 1 to 10 wt. % of a fatty acyl isethionate product which product comprises 40 to 80 wt. % fatty acyl isethionate and 15 to 50 wt. % free fatty acid and/or fatty acid salt; and, e) from 0.1 to 5 wt. % of cocamidopropyl betaine.

DETAILED DESCRIPTION OF THE INVENTION

Fatty Acyl Isethionate Product

The fatty acyl isethionate product is present at a level of from 1 to 10 wt. %, preferably from 2 to 8 wt. %, more preferably from 2.5 to 7.5 wt. %.

The preferred fatty acyl isethionate product comprises fatty acyl isethionate surfactant at a level of from 40 to 80 wt. % of the product, as well as free fatty acid and/or fatty acid salt at a level of from 15 to 50%.

Preferably, greater than 20 wt. % and less than 45 wt. %, more preferably greater than 25 wt. % and less than 45 wt. % of the fatty acyl isethionate are of chain length greater than or equal to $C_{16}$; and greater than 50 wt. %, preferably greater than 60 wt. % of the free fatty acid/soap is of chain length $C_{16}$ to $C_{20}$.

The fatty acyl isethionate surfactant component is typically prepared by the reaction of an isethionates salt such as alkali metal isethionates and an aliphatic fatty acid having 8 to 20 carbon atoms and Iodine Value (measuring degree of unsaturation) of less than 20 g, for example:

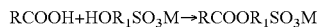

where $R_1$ is an aliphatic hydrocarbon radical containing 2 to 4 carbons; M is alkali metal cation or metal ion (e.g., sodium, magnesium, potassium, lithium), ammonium or substituted ammonium cation or other counterion; and, R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates (which formed from the reaction) and 50 to about 15 wt. %, typically 40 to 20 wt. % of free fatty acids. In addition, the product may contain isethionates salts which are present typically at levels less than 5 wt. %, and traces (less than 2 wt. %) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) preferably should have more than 20 wt. %, preferably more than 25 wt. %, but no more than 45 wt. %, preferably 35% (on basis of fatty acyl isethionates reaction product) of fatty acyl group with 16 or greater carbon atoms to provide both excellent lather and mildness of the resulting fatty acyl isethionate product. These longer chain fatty acyl isethionate surfactants and fatty acids, i.e. fatty acyl group and fatty acid with 16 or more carbons, can typically form insoluble surfactant/fatty acid crystals in water at ambient temperatures.

Examples of commercial fatty acyl isethionate products that are particularly useful in the subject invention are DEFI flakes and Dove® cleansing bar noodles produced by Unilever. DEFI (Direct Esterification of Fatty Isethionate) flakes typically contain about 68 to 80 wt. % of sodium fatty acyl isethionate and 15 to 30 wt. % free fatty acid. More than 25 wt. % and no more than 35% of fatty acyl group of the resulting fatty acyl isethionate have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt. % of fatty acyl isethionate and 30 to 40 wt. % of fatty acid and fatty soap.

Zinc Active

The anti-dandruff shampoo comprises an antidandruff zinc salt. The anti-dandruff zinc salts may be selected from zinc pyrithione, zinc sulfate and hydrates thereof (e.g. zinc sulfate hexahydrate), and combinations. Zinc pyrithione (ZnPTO) which is an alternate name for zinc 1-hydroxy-2-pyridinethione is preferred.

The anti-dandruff zinc salt is present at a level of from 0.1 to 5 wt. %, preferably from 0.2 to 3 wt. %, more preferably from 0.25 to 2.5 wt. % based on the anti-dandruff shampoo composition.

Other AD Actives

Additional anti-dandruff actives may be included in the compositions. Illustrative substances are octopirox (piroctone olamine), azole antimicrobials (e.g. climbazole), selenium sulfide and combinations thereof. Amounts of these materials may range from about 0.01 to about 5 wt. %, preferably from 0.1 to 3 wt. %, and optimally from about 0.3 to about 4 wt. % of the composition.

Glycinate

The anti-dandruff shampoo comprises from 1 to 8 wt. %, preferably from 2 to 6 wt. % of an alkyl glycinate and/or alkyl carboxyglycinate.

Preferably the alkyl glycinate and/or alkyl carboxyglycinate has an alkyl group of from $C_{8-22}$ carbon atoms, in the form of a salt with a solubilising cation such as sodium, potassium, ammonium or substituted ammonium. Preferred glycinates are sodium coco glycinate and sodium cocoyl glycinate.

Anionic Cleansing Surfactant.

The anti-dandruff shampoo comprises an alkyl sulphate and/or ethoxylated alkyl sulfate anionic surfactant at a level of from 2 to 16 wt. %, preferably from 3 to 14 wt. %, more preferably from 4 to 10 wt. %.

Preferred alkyl sulfates are $C_{8-18}$ alky sulfates, more preferably $C_{12-18}$ alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: $RO(CH_2CH_2O)_n SO_3M$; wherein R is an alkyl or alkenyl having from 8 to 18 (preferably 12 to 18) carbon atoms; n is a number having an average value of greater than at least 0.5, preferably between 1 and 3; and M is a solubilising cation such as sodium, potassium, ammonium or substituted ammonium. An example is sodium lauryl ether sulfate (SLES).

A preferred ethoxylated alkyl sulfate anionic surfactant is sodium lauryl ether sulfate (SLES) having an average degree of ethoxylation of from 0.5 to 3, preferably 1 to 3.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

If added, the total amount of additional anionic cleansing surfactant in shampoo compositions of the invention may generally range from 0.5 to 45 wt. %, preferably from 1.5 to 35 wt. %, more preferably from 5 to 20 wt. %, calculated by total weight anionic cleansing surfactant based on the total weight of the composition.

The composition can include co-surfactants, to help impart aesthetic, physical or cleansing properties to the composition.

An example of a co-surfactant is a nonionic surfactant, which can be included in an amount ranging from 0.5 to 8%, preferably from 2 to 5% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more; preferably, the value of n lies from about 1.1 to about 2; most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92/06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.1 to about 10 wt. %, preferably from 0.5 to 8, more preferably from 1 to 5 wt. %, based on the total weight of the composition.

Examples of amphoteric or zwitterionic surfactants include alkyl amine oxides, alkyl betaines, alkyl amidopropyl betaines, alkyl sulphobetaines (sultaines), alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 50%, preferably from 2 to 40%, more preferably from 10 to 25% by total weight surfactant based on the total weight of the composition.

Silicone

Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Number average particle size diameters for the silicones may range from about 0.01 micron to about 50 micron, most preferably from about 0.01 to about 0.5 micron.

Advantageously the compositions of this invention may include a pre-mix of a silicone microemulsion. The microemulsion is an aqueous surfactant stabilized emulsion of silicone particles having a number average particle diameter ranging from about 10 to about 1,000 nm, preferably from about 100 to about 500 nm.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions or microemulsions of dimethiconol. Also suitable are amodimethicone emulsions such as DC939 (from Dow Corning) and SME253 (from GE Silicones). Amounts of the silicone in compositions where present may range from about 0.01 to about 10 wt. %, preferably from about 0.1 to about 8 wt. %, more preferably from about 0.3 to about 5 wt. % by weight of the shampoo compositions.

Cationic Polymer

A cationic polymer is an optional, but preferred ingredient in shampoo compositions according to the invention, for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl(meth)acrylamides, alkyl(meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and copolymers of unsaturated carboxylic acids having from 3 to 5 carbon atoms, (as described in U.S. Pat. No. 4,009, 256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

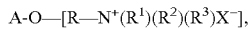

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C135, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 percent by weight of the composition.

When cationic conditioning polymer is present in a shampoo composition according to the invention, it is preferred if the copolymer is present as emulsion particles with a mean diameter ($D_{3,2}$ as measured by light scattering using a Malvern particle sizer) of 2 micrometers or less.

Shampoo compositions of the invention are preferably aqueous, i.e. they have water or an aqueous solution or a lyotropic liquid crystalline phase as their major component. Suitably, the composition will comprise from 50 to 98%, preferably from 60 to 90% water by weight based on the total weight of the composition.

Suspending Agent

Preferably a shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent, if included, will generally be present in a shampoo composition of the invention at levels of from 0.1 to 10%, preferably from 0.5 to 6%, more preferably from 0.9 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The Examples will now be illustrated with reference to the following non-limiting Examples. Inventions according to the invention are demonstrated by a number, comparative inventions are demonstrated by a letter.

EXAMPLES

The advantage of the invention will be demonstrated by the following examples. The effect of the inventive formulations in relation to improvement of the skin stratum corneum barrier will be shown by a forearm controlled application test (FCAT) with the following measurements taken before application (as a baseline) and after the final test:
a) visual dryness assessment;
b) trans epidermal water loss (TEWL); and,
c) corneometer measurement The FCAT test involved 16 people and involved taking a baseline measurement for parameters a), b) and c); treatment with a control product (formulation A), and a product according to the invention (formulation 1) over 2 days with 3 wash sessions of 2 product applications per day a minimum of 2 hrs apart (giving 6 applications of product per day in total). The sites were washed for 10 seconds, with 90 seconds lather retention and rinsed for 15 seconds. The final measurement was taken on the $3^{rd}$ day~19 hrs post final product application.

Formulations Tested

The formulation used in the test procedure is also shown as example I of the formulation list, compared against a standard SLES/ZnPTO anti-dandruff shampoo—the main ingredients of these are shown below:

| INCI name | Tradename | Control 'A' wt. % | Ex 1 wt. % |
|---|---|---|---|
| Sodium Laureth Sulfate | Texapon N701 | 14.0 | 6.0 |
| Cocamidopropyl Betaine | Tegobetaine CK | 1.6 | 3.0 |
| Fatty Acyl Isethionate Product[1] | | — | 2.0 |
| Sodium cocoyl glycinate | Hostapon SG | — | 4.0 |
| Zinc Pyrithione | Zinc Omadine FPS | 1.0 | 1.0 |

[1]The Fatty Acyl Isethionate product is Sodium Cocoyl isethionate, Stearic Acid, Coconut Fatty Acid, Sodium Isethionate and Water produced in-house by Unilever Formulation 1 was compared in a straight blind comparison against a control formulation 'A' in relation to the skin stratum corneum barrier measurements:
a) visual dryness assessment;
b) trans epidermal water loss (TEWL); and,
c) corneometer measurement The visual dryness assessment was made by a trained assessor; a lower value indicates a better score—indicating less dryness.

Trans epidermal water loss was measured on an Instrumental ServoMed, a lower value for TEWL indicates an improved (stronger) skin stratum corneum barrier because less water is lost across the skin barrier.

The corneometer measures capacitance, this is a measure of skin hydration, a higher level shows better skin hydration, this is indicative of an improved condition of the skin stratum corneum barrier (or a skin barrier that is less damaged), this value was measured on a Corneometer CM 825 supplied by Courage+Khazaka electronic GmbH.

Example 1

| Skin barrier condition measurement | Control | Ex. 1 |
|---|---|---|
| Visual Dryness Assessment (Assessor score) | 1.55 | 0.85 |
| Trans epidermal water loss ($g/m^2/h$) | 3.52 | 1.55 |
| Corneometer measurement (arbitrary units) | −5.84 | −1.00 |

In each case the formulation of example 1 provides a better value, indicating an improvement in the condition of the skin stratum corneum barrier. For all three tests, the scores were significantly different ($p<0.05$, Fishers LSD) between the control formulation 'A' and formulation 1.

These tests show that a surfactant system including a combination of fatty acyl isethionate product and an alkyl glycinate and/or alkyl carboxyglycinate provides an improvement to the condition of the skin stratum corneum barrier. This will provide improved anti-dandruff shampoos.

Example Formulations

| INCI name | Tradename | Ex I wt. % | Ex II wt. % | Ex III wt. % | Ex IV wt. % |
|---|---|---|---|---|---|
| Sodium Laureth Sulfate | Texapon N70 | 3.0 | 6.0 | 2.0 | 4.0 |
| Cocamidopropyl Betaine | Tegobetaine CK | 3.0 | 1.6 | 3.0 | 2.0 |
| Fatty Acyl Isethionate Product[1] | | 2.0 | 3.0 | 6.0 | 5.0 |

-continued

| INCI name | Tradename | Ex I wt. % | Ex II wt. % | Ex III wt. % | Ex IV wt. % |
|---|---|---|---|---|---|
| Sodium cocoyl glycinate | Hostapon SG | 4.0 | 4.0 | 5.0 | 4.0 |
| Acrylates/ Streareth-20 Methacrylate polymer | Aculyn 88 | 1.0 | 1.0 | 0.75 | 1.0 |
| Silicone Emulsion[2] | | 3.0 | 2.0 | 3.0 | 2.0 |
| Guar Hydroxy-propyltrimonium Chloride | Cesmetic BF-7 | 0.25 | 0.25 | 0.25 | 0.25 |
| Zinc Pyrithione | Zinc Omadine FPS | 1.0 | 1.0 | 1.0 | 1.0 |
| Fragrance | | 0.75 | 0.75 | 0.75 | 0.75 |
| Aqua + minors | | to 100 | to 100 | to 100 | to 100 |

[1]The Fatty Acyl Isethionate product is Sodium Cocoyl isethionate, Stearic Acid, Coconut Fatty Acid, Sodium Isethionate and Water produced in-house by Unilever
[2]Mixture of silicone emulsions from Wacker and Dow

The invention claimed is:

1. An anti-dandruff shampoo comprising: —
   a) from 0.1 to 5 wt. % of an anti-dandruff zinc salt;
   b) from 1 to 8 wt. % of an alkyl glycinate and/or alkyl carboxyglycinate;
   c) from 2 to 16 wt. % of an alkyl sulphate and/or ethoxylated alkyl sulfate anionic surfactant; and,
   d) from 1 to 10 wt. % of a fatty acyl isethionate product which product comprises 40 to 80 wt. % fatty acyl isethionate and 15 to 50 wt. % free fatty acid and/or fatty acid salt.

2. A shampoo according to claim 1, wherein the anti-dandruff zinc salt is zinc pyrithione (ZnPTO).

3. A shampoo according to claim 1, wherein the anti-dandruff zinc salt is present at a level of from 0.25 to 2.5 wt. %.

4. A shampoo according to claim 1, wherein the alkyl sulfate and/or ethoxylated alkyl sulfate anionic surfactant comprises from 3 to 12 wt. %, preferably from 4 to 10 wt. % of sodium lauryl ether sulfate having an average degree of ethoxylation of from 0.5 to 3.

5. A shampoo according to claim 1, wherein the alkyl glycinate and/or alkyl carboxyglycinate is present at a level of from 1 to 8 wt. %, preferably from 2 to 6 wt. %, and has an alkyl group comprising of from $C_{8-22}$ carbon atoms, wherein the glycinate is in the form of a salt with a solubilising cation such as sodium, potassium, ammonium or substituted ammonium.

6. A shampoo according to claim 1, wherein the glycinate is sodium alkyl carboxylglycinate having an alkyl group of from $C_{8-22}$ carbon atoms.

7. A shampoo according to claim 1, additionally comprising from 0.1 to 10 wt. % of a betaine surfactant, preferably an alkyl amidopropyl betaine.

8. A shampoo according to claim 1, additionally comprising from 0.1 to 5 wt. % of a cationic polymer, preferably a cationic polysaccharide polymer.

9. A shampoo according to claim 1, comprising: —
   a) from 0.25 to 2.5 wt. % of zinc pyrithione;
   b) from 2 to 6 wt. % of sodium alkyl carboxylglycinate having an alkyl group of from $C_{8-22}$ carbon atoms;
   c) from 4 to 10 wt. % of sodium lauryl ether sulfate having an average degree of ethoxylation of from 0.5 to 3;
   d) from 1 to 10 wt. % of a fatty acyl isethionate product which product comprises 40 to 80 wt. % fatty acyl isethionate and 15 to 50 wt. % free fatty acid and/or fatty acid salt; and,
   e) from 0.1 to 5 wt. % of cocamidopropyl betaine.

* * * * *